US011246959B2

(12) United States Patent
Johnson (10) Patent No.: US 11,246,959 B2
(45) Date of Patent: Feb. 15, 2022

(54) BIOCOMPATIBLE FIBER TEXTILES FOR IMPLANTATION

(71) Applicant: NANOFIBER SOLUTIONS, LLC, Dublin, OH (US)

(72) Inventor: Jed K. Johnson, London, OH (US)

(73) Assignee: NANOFIBER SOLUTIONS, LLC, Dublin, OH (US)

( * ) Notice: Subject to any disclaimer, the term of this patent is extended or adjusted under 35 U.S.C. 154(b) by 0 days.

(21) Appl. No.: 16/904,097

(22) Filed: Jun. 17, 2020

(65) Prior Publication Data
US 2021/0138108 A1 May 13, 2021

Related U.S. Application Data

(63) Continuation of application No. 14/216,976, filed on Mar. 17, 2014, now abandoned.

(60) Provisional application No. 61/798,265, filed on Mar. 15, 2013.

(51) Int. Cl.
| A61L 27/14 | (2006.01) |
|---|---|
| D01D 5/00 | (2006.01) |
| D06M 23/08 | (2006.01) |
| A61L 27/26 | (2006.01) |
| A61L 27/50 | (2006.01) |
| C08L 75/04 | (2006.01) |

(52) U.S. Cl.
CPC ........... *A61L 27/14* (2013.01); *A61L 27/26* (2013.01); *A61L 27/50* (2013.01); *D01D 5/0076* (2013.01); *D06M 23/08* (2013.01); *A61L 2400/12* (2013.01); *A61L 2430/22* (2013.01); *C08L 75/04* (2013.01); *Y10T 428/1362* (2015.01)

(58) Field of Classification Search
CPC .. A61L 2400/12; A61L 2430/22; A61L 27/26; A61L 27/50; C08L 75/04; Y10T 428/1362; D01D 5/0076
See application file for complete search history.

(56) References Cited

U.S. PATENT DOCUMENTS

| 4,693,721 A | 9/1987 | Ducheyne |
|---|---|---|
| 4,738,740 A | 4/1988 | Pinchuk et al. |
| 5,258,027 A | 11/1993 | Berghaus |
| 5,628,788 A | 5/1997 | Pinchuk |
| 6,143,022 A | 11/2000 | Shull et al. |
| 6,143,293 A | 11/2000 | Weiss et al. |
| 6,147,135 A | 11/2000 | Yuan et al. |
| 6,592,623 B1 | 7/2003 | Bowlin et al. |
| 7,115,220 B2 | 10/2006 | Dubson et al. |
| 7,172,765 B2 | 2/2007 | Chu et al. |
| 7,220,281 B2 | 5/2007 | Lambrecht et al. |
| 7,390,760 B1 | 6/2008 | Chen et al. |
| 7,490,563 B2 | 2/2009 | Eastin et al. |
| 7,629,030 B2 | 12/2009 | Robertson et al. |
| 7,718,351 B2 | 5/2010 | Ying et al. |
| 7,993,567 B2 | 8/2011 | Scott-Carnell et al. |
| 8,157,722 B2 | 4/2012 | Arnal et al. |
| 8,222,166 B2 | 7/2012 | Chu et al. |
| 8,728,463 B2 | 5/2014 | Atala et al. |
| 9,334,476 B2 | 5/2016 | Arinzeh et al. |
| 9,771,557 B2 | 9/2017 | Arinzeh et al. |
| 10,080,687 B2 | 9/2018 | MacEwan |
| 10,562,225 B2 | 2/2020 | Johnson |
| 10,617,512 B2 | 4/2020 | MacEwan et al. |
| 10,632,228 B2 | 4/2020 | MacEwan |
| 10,682,444 B2 | 6/2020 | MacEwan |
| 10,888,409 B2 | 1/2021 | MacEwan et al. |
| 2002/0082707 A1 | 6/2002 | Homsy |
| 2002/0090725 A1 | 7/2002 | Simpson et al. |
| 2002/0142458 A1 | 10/2002 | Williams et al. |
| 2003/0168756 A1 | 9/2003 | Balkus et al. |
| 2003/0211130 A1* | 11/2003 | Sanders .................. A61L 27/34 424/423 |
| 2003/0226750 A1 | 12/2003 | Fenn |
| 2004/0037813 A1 | 2/2004 | Simpson et al. |
| 2005/0177249 A1 | 8/2005 | Kladakis et al. |

(Continued)

FOREIGN PATENT DOCUMENTS

| AU | 2009207489 B2 | 9/2014 |
|---|---|---|
| CN | 101123930 A | 2/2008 |

(Continued)

OTHER PUBLICATIONS

Macchiarini et al. "Clinical Transplantation of a Tissue-Engineered Airway" (Dec. 13, 2008) The Lancet 372 (9655):2023-2030.
Martins et al. "Electrospun nanostructured scaffolds for tissue engineering applications" (2007) Nanomedical 2(6):929-942.
Mathews "Preparation and anisotropic mechanical behavior of highly-oriented electrospun poly(butylene terephthalate) fibers" (Aug. 2006) Journal of Applied Polymer Science 101(3):2017-2021.
McClure et al. "A Three-Layered Electrospun Matrix to Mimic Native Arterial Architecture Using Polycaprolactone, Elastin, and Collagen: A Preliminary Study" (2010) Acta Biomaterialia 6:2422-2433.

(Continued)

*Primary Examiner* — Anna R Falkowitz
(74) *Attorney, Agent, or Firm* — Troutman Pepper Hamilton Sanders LLP (57) ABSTRACT

A biocompatible textile and methods for its use and fabrication are disclosed. The textile may be fabricated from electrospun fibers forming windings on a mandrel, in which the windings form openings having a mesh size between adjacent windings. The textile may also be fabricated by the addition of solvent-soluble particles incorporated into the textile while the windings are formed. Such particles may be removed by exposing the textile to a solvent, thereby dissolving them. Disclosed are also replacements for animal organs composed of material including at least one layer of an electrospun fiber textile having a mesh size. Such replacements for animal organs may include biocompatible textiles treated with a surface treatment process.

12 Claims, 3 Drawing Sheets

(56) References Cited

U.S. PATENT DOCUMENTS

| | | |
|---|---|---|
| 2005/0220848 A1 | 10/2005 | Bates |
| 2005/0277985 A1 | 12/2005 | Wert et al. |
| 2006/0060999 A1 | 3/2006 | Amagasa et al. |
| 2006/0085063 A1 | 4/2006 | Shastri et al. |
| 2006/0128012 A1 | 6/2006 | Arinzeh et al. |
| 2006/0134157 A1 | 6/2006 | Lehman et al. |
| 2006/0135020 A1 | 6/2006 | Weinberg et al. |
| 2006/0154063 A1 | 7/2006 | Fujihara et al. |
| 2006/0204539 A1 | 9/2006 | Atala et al. |
| 2007/0142907 A1* | 6/2007 | Moaddeb ............... A61F 2/2469 623/2.11 |
| 2007/0191956 A1 | 8/2007 | Prewett et al. |
| 2007/0218118 A1 | 9/2007 | Michal et al. |
| 2007/0232169 A1 | 10/2007 | Strickler et al. |
| 2007/0269481 A1 | 11/2007 | Li et al. |
| 2007/0286880 A1 | 12/2007 | Vasiliev et al. |
| 2008/0208323 A1 | 8/2008 | El-Kurdi et al. |
| 2008/0208358 A1 | 8/2008 | Bellamkonda et al. |
| 2009/0018643 A1 | 1/2009 | Hashi et al. |
| 2009/0074832 A1 | 3/2009 | Zussman et al. |
| 2009/0108503 A1 | 4/2009 | Scott-Carnell et al. |
| 2009/0143855 A1 | 6/2009 | Weber et al. |
| 2009/0152773 A1 | 6/2009 | Barinov et al. |
| 2009/0162468 A1 | 6/2009 | Barinov et al. |
| 2009/0208577 A1 | 8/2009 | Xu et al. |
| 2009/0253328 A1 | 10/2009 | Watanabe et al. |
| 2010/0082114 A1 | 4/2010 | Gingras et al. |
| 2010/0105799 A1 | 4/2010 | Rudd et al. |
| 2010/0166854 A1 | 7/2010 | Michniak-Kohn et al. |
| 2010/0222771 A1 | 9/2010 | Mitchell et al. |
| 2010/0233115 A1 | 9/2010 | Patel et al. |
| 2010/0273258 A1 | 10/2010 | Lannutti et al. |
| 2010/0303881 A1 | 12/2010 | Hoke et al. |
| 2011/0022149 A1 | 1/2011 | Cox et al. |
| 2011/0028834 A1 | 2/2011 | Zussman |
| 2011/0030885 A1 | 2/2011 | Anneaux et al. |
| 2011/0070283 A1 | 3/2011 | Hossainy et al. |
| 2011/0083987 A1 | 4/2011 | Rolland et al. |
| 2011/0098826 A1 | 4/2011 | Mauck et al. |
| 2011/0166647 A1 | 7/2011 | Hashi et al. |
| 2011/0177395 A1 | 7/2011 | Kamisasa |
| 2011/0270412 A1 | 11/2011 | Bellan et al. |
| 2012/0068384 A1 | 3/2012 | Phaneuf et al. |
| 2012/0093717 A1 | 4/2012 | Mauck et al. |
| 2012/0271405 A1 | 10/2012 | Soletti et al. |
| 2013/0052254 A1 | 2/2013 | Arinzeh et al. |
| 2013/0095165 A1 | 4/2013 | Olson et al. |
| 2013/0103079 A1 | 4/2013 | Lau et al. |
| 2013/0150963 A1 | 6/2013 | Johnson |
| 2013/0245784 A1 | 9/2013 | Tan et al. |
| 2013/0310920 A1 | 11/2013 | Su |
| 2013/0338791 A1 | 12/2013 | McCullen et al. |
| 2014/0030315 A1 | 1/2014 | Johnson |
| 2014/0057346 A1 | 2/2014 | Johnson |
| 2014/0072951 A1 | 3/2014 | Johnson |
| 2014/0079759 A1 | 3/2014 | Patel et al. |
| 2014/0107700 A1 | 4/2014 | Baird et al. |
| 2014/0107803 A1 | 4/2014 | Grosse |
| 2014/0142718 A1 | 5/2014 | Seyedin et al. |
| 2014/0309726 A1 | 10/2014 | Wang |
| 2015/0010607 A1 | 1/2015 | Francis et al. |
| 2015/0110846 A1 | 4/2015 | Yu et al. |
| 2016/0022873 A1 | 1/2016 | Besner et al. |
| 2016/0024690 A1 | 1/2016 | Francis et al. |
| 2016/0143745 A1 | 5/2016 | Kandel et al. |
| 2016/0317706 A1 | 11/2016 | Johnson |
| 2017/0182206 A1 | 6/2017 | Johnson et al. |
| 2019/0249127 A1 | 8/2019 | Johnson |

FOREIGN PATENT DOCUMENTS

| | | | |
|---|---|---|---|
| CN | 101406711 | A | 4/2009 |
| CN | 102008755 | * | 4/2011 |
| CN | 102008755 | A | 4/2011 |
| CN | 102493020 | A | 6/2012 |
| CN | 102908677 | A | 2/2013 |
| EP | 0416846 | A2 | 3/1991 |
| EP | 2422003 | A1 | 2/2012 |
| JP | 20115009786 | A | 3/2011 |
| JP | 2012505320 | A | 3/2012 |
| JP | 2012527217 | A | 11/2012 |
| JP | 2013031595 | A | 2/2013 |
| WO | 2000010622 | A1 | 3/2000 |
| WO | 2001015754 | A1 | 3/2001 |
| WO | 2005012606 | A2 | 2/2005 |
| WO | 2005096989 | A1 | 10/2005 |
| WO | 2006138552 | A2 | 12/2006 |
| WO | 2008137659 | A1 | 11/2008 |
| WO | 2009089035 | A1 | 7/2009 |
| WO | 2010040129 | A2 | 4/2010 |
| WO | 2010048281 | A1 | 4/2010 |
| WO | 2010124207 | A1 | 10/2010 |
| WO | 2013025819 | A2 | 2/2013 |
| WO | 2013078051 | A1 | 5/2013 |
| WO | 2013106822 | A1 | 7/2013 |
| WO | 2014031721 | A1 | 2/2014 |
| WO | 2014145864 | A1 | 9/2014 |
| WO | 2015153011 | A1 | 10/2015 |

OTHER PUBLICATIONS

Meng et al. "Electrospun aligned nanofibers composite of MWCNT/polyurethane to enhance vascular endothelium cells proliferation and function" (Jul. 8, 2010) Journal of Nanoscience and Nanotechnology, pp. 312-320.

Mori et al. "Fibrocytes contribute to the myofibroblast population in wounded skin and originate from the bone marrow" (Mar. 10, 2005) Experimental Cell Research 304(1):81-90.

Nam et al. "Improved Cellular Infiltration in Electrospun Fiber via Engineered Porosity" (Sep. 2007) Tissue Engineering 13(9):2249-2257.

Nam et al. "Materials selection and residual solvent retention in biodegradable electrospun fibers" (Feb. 5, 2008) Journal of Applied Polymer Science 107(3):1547-1554.

Nam et al. "Modulation of Embryonic Mesenchymal Progenitor Cell Differentiation via Control Over Pure Mechanical Modulus in Electrospun Nanofibers" (Apr. 2011) Acta Biomaterialia 7(4):1516-1524.

Nam et al. "Novel Electrospun Scaffolds for the Molecular Analysis of Chondrocytes Under Dynamic Compression" (200), Tissue Engineering Part A 15(3):513-523.

Park, "Lab-made organ implanted for first time" (Jul. 14, 2017), CNN.com <http://www.cnn.com/2011/HEALTH/07/07/trachea.transplant/index.html>.

Pham et al. "Electrospinning of Polymeric Nanofibers for Tissue Engineering Applications: A Review" (2006) Tissue Engineering 12(5):1197-1211.

Powell et al. "EDC cross-linking improves skin substitute strength and stability" (2006) Biomaterials 27(34):5821-5827.

Reneker et al. "Nanometre diameter fibres of polymer, produced by electrospinning" (1996) Nanotechnology 7(3):216-223.

Ruoslahti "Brain extracellular matrix" (1996) Glycobiolyghy 6(5):489-492.

Samios et al., "In situ compatibilization of polyurethane with poly(ethylene terephthalate)," Department of Chemistry, European Polymer Journal (2000), 36 pp. 937-947.

Shin et al. "Contractile cardiac grafts using a novel nanofibrous mesh" (Aug. 2004) Biomaterials 25(17):3717-3723.

Shin et al. "In Vivo Bone Tissue Engineering Using Mesenchymal Stem Cells on a Novel Electrospun Nanofibrous Scaffold" (Jul. 9, 2004) Tissue Engineering 10(1-2):33-41.

Srikar et al. "Desorption-limited mechanism of release from polymer nanofibers" (2008) Langmuir 24(3):965-974.

Stitzel et al. "Controlled Fabrication of a Biological Vascular Substitute" (2006) Biomaterials 27:1088-1094.

Supplemental European Search Report and Written Opinion for EP15774154 dated Sep. 22, 2017.

(56) References Cited

OTHER PUBLICATIONS

Teo et al. "A review on electrospinning design and nanofibre assemblies" (2006) Nanotechnology 17(14):R89-R106.
Teo et al. "Electrospun fibre bundle made of aligned nanofibers over two fixed points" (1978) Nanotechnology 16:1878-1884.
Tse, et al. "Current Status of Pipeline Embolization Device in the Treatment of Intracranial Aneurysms: A review" (Dec. 2013) World Neurosurgery 80(6): 829-835.
Wang et al. "Nanofibres and their Influence on Cells for Tissue Regeneration" (2005) Aust. J. Chem. 58(10):704-712.
Xie et al. "Encapsulation of protein drugs in biodegradable microparticles by co-axial electrospray" Jan. 15, 2008) Journal of Colloid and Interface Science 317(2):469-476.
Yoo et al. "Surface-Functionalized Electrospun Nanofibers for Tissue Engineering and Drug Delivery" Jan. 1, 2009, Advanced Drug Delivery Reviews 61:1033-1042.
Yoshimoto et al. "A biodegradable nanofiber scaffold by electrospinning and its potential for bone tissue engineering" (May 2003) Biomaterials 24(12):2077-2082.
Yu et al. "Production of submicrometer diameter fibers by two-fluid electrospinning" (Sep. 2004) Adv. Mater. 16(17):1562-1566.
Zeng et al. "Enzymatic degradation of poly(L-lactide) and poly(e-caprolactone) electrospun fibers" (Dec. 15, 2004) Macromolecular Bioscience 4(12):1118-1125.
Zeng et al. "Ultrafine fibers electrospun from biodegradable polymers" (Jul. 25, 2003) Journal of Applied Polymer Science 89(4):1085-1092.
Zhang et al. "Electrospinning of gelatin fibers and gelatin/PCL composite fibrous scaffolds" (2005) J. Biomed. Mater. Res. Part B: Appl. Biomater. 72B(1):156-165.
Zhang et al. "Recent development of polymer nanofibers for biomedical and biotechnological applications" (2005) Journal of Materials Science-Materials in Medicine 16(10):933-946.
Zhu et al. "Characterization of a co-electrospun scaffold of HLC/CS/PLA for vascular tissue engineering" 2014, Biio-Medical Mat. Engin. 24(6):1999-2005.
Ayres et al. "Microvascular Endothelial Cell Migration in Scaffolds of Electrospun Collagen" (Mar. 2005) Wound Repair and Regeneration 13(2):A6 (abstract only).
Baker et al. "The Potential to Improve Cell Infiltration in Composite Fiber-aligned Electrospun Scaffolds by the Selective Removal of Sacrificial Fibers" May 2008, Biiomaterials 29(15):2248-2358.
Barnhart et al. "Evaluation of an intra-articular synthetic ligament for treatment of cranial cruciate ligament disease in dogs: a six-month prospective clinical trial" Jun. 2016, Vet Comp Orthop. Traumatol. 29:491-498.
Bershadsky et al. "Adhesion-mediated mechanosensitivity: a time to experiment, and a time to theorize" (Oct. 2006) Curr. Opn. Cell Biol. 18(5):472-481.
Bucala et al. "Circulating Fibrocytes Define A New Leukocyte Subpopulation That Mediates Tissue Repair" (Nov. 1994) Mol. Med. 1(1):71-81.
Cattaruzza et al. "Proteoglycan control of cell movement during wound healing and cancer spreading" (Sep. 2005) Matrix Biol. 24(6):400-417.
Chen et al. "Preparation and Characterization of Coaxial Electrospun Thermoplastic Polyurethane/Collagen Compound Nanofibers for Tissue Engineering Applications" (2010) Colloids and Surfaces B-Biointerfaces 79(2):315-325.
Chew et al. "The Role of Electrospinning in the Emerging Field of Nanomedicine" (2006) Curr. Pharm. Sec. 12(36) A:4751-4770.
Choi et al. "Structuring electrospun polycaprolactone nanofiber tissue scaffolds by femtosecond laser ablation" (Nov. 2007) J. Laser Appl. 19(4):225-231.
Cukierman et al. "Taking cell-matrix adhesions to the third dimension" (Nov. 23, 2001) Science 294:1708-1712.
Diaz et al. "Controlled encapsulation of hydrophobic liquids in hydrophilic polymer nanofibers by co-electrospinning" (2006) Adv. Funct. Mater. 16(16):2110-2116.

Discher et al. "Tissue cells feel and respond to the stiffness of their substrate" (Nov. 18, 2005) Science 310:1139-1143.
Drilling et al. "Fabrication of burst pressure competent vascular grafts via electrospinning: Effects of microstructure" (Mar. 15, 2009) J. Miomed. Mat. Res. Part A 88A(4):923-934.
Duling et al. "Mechanical characterization of electrospun Polycaprolactone (PCL): a potential scaffold for tissue engineering" (Feb. 2008) J. Biomech. Eng. 130(1) No. 011006.
Engler et al. "Matrix Elasticity Directs Stem Cell Lineage Specification" (Aug. 25, 2006) Cell 126(4):677-689.
Frey et al. "Electrospinning and Porosity Measurements of Nylon6 PEO blended Nonwovens" (2007) Journal of Engineered Fibers and Fabrics 2(1):31-37.
Fujihara et al. "Guided bone regeneration membrane made of Polycaprolactone/calcium carbonate composite nano-fibers" (Jul. 2005) Biomaterials 26(19):4139-4147.
Gaumer et al. "Structure-function relationships and Source-to-ground Distance and the Mechanical Properties of Electrospun Fiber" (2009) Acta Biomaterialia 5(5):1552-1561.
Hashi et al. "Antithrombogenic Modification of Small Diameter Microfibrous Vascular Grafts" (Aug. 2010) Arterioscler Thromb Vase Biol. 30(8):1621-1627.
Hashi et al. "Antithrombogenic Property of Bone Marrow Mesenchymal Stem Cells in Nanofibrous Vascular Grafts" (Jul. 17, 2007) PNAS 104(29): 11915-11920.
He et al. "Fabrication of Drug-Loaded Electrospun Aligned Fibrous Threads for Suture Applications" 2009, J. Biomed. Mater. Research, Part A 89(1):80-95.
Herrera et al. "Randomly Oriented and Aligned Cellulose Fibres Reinforced with Cellulose Nanowhiskers, Prepared by Electrospinning" 2011, Plastics, Rubber and Composites 40(2):57-64.
Hsu et al. "N,N-Dimethylformamide Additions to the Solution for the Electrospinning of Poly(e-caprolactone) Nanofibers" (Apr. 2004) Macromolecular Materials and Engineering 289(4):334-340 (Abstract only).
Hsu et al. "Nano-sized beads and porous fiber constructs of Poly(e-caprolactone) produced by electrospinning" (2004) Journal of Material Science 39(9):3003-3013.
Huang et al. "A review on polymer nanofibers by electrospinning and their applications in nanocomposites" (Nov. 2003) Composites Science and Technology 63(15):2223-2253.
International Search Report and Written Opinion for PCT/US2013/055941 dated Nov. 12, 2013.
International Search Report and Written Opinion for PCT/US2015/016973 dated May 22, 2015.
International Search Report and Written Opinion for PCT/US2016/030058 dated Jul. 29, 2016.
International Search Report and Written Opinion for PCT/US2016/60157 dated Jan. 31, 2017.
International Search Report and Written Opinion for PCT/US2018/064570 dated Feb. 6, 2019.
Johnson "First-in-the-World Equine Joint Injection for Osteoarthritis" (Jul./Aug. 2014) The International Equine Veterinarian 23-25.
Johnson et al. "Electrospun PCL in Vitro: a Microstructural Basis for Mechanical Property Changes" (2009) Journal of Biomaterials Science, Polymer Edition 20(4):467-481.
Johnson et al. "Microstructure-Property Relationships in a Tissue-Engineering Scaffold" (2007) Journal of Applied Polymer Science 104(5):2919-2927.
Johnson et al. "Quantitative Analysis of Complex Glioma Cell Migration on Electrospun Polycaprolcatone Using Time-Lapse Microscopy" (2009) Tissue Engineering Part C 15(4):531-540.
Kang et al. "Plasma Treatment of Textiles—synthetic Polymer-Base Textiles" (2004) AATCC Review 4(11):29-33.
Katta et al. "Continuous electrospinning of aligned polymer nanofibers onto a wire drum collector" (Sep. 28, 2004) Nano Letters 4(11):2215-2218.
Kazemnejad et al. "Biochemical and Molecular Characterization of Hepatocyte-Like Cells Derived from Human Bone Marrow Mesenchymal Stem Cells on a Novel Three-Dimensional Biocompatible Nanofibrous Scaffold" (Feb. 1, 2009) J. Gastronenter. Hepatol. 24(2):278-287.

(56) References Cited

OTHER PUBLICATIONS

Khil et al. "Novel fabricated matrix via electrospinning for tissue engineering" (2005) Journal of Biomedical Materials Research Part B—Applied Biomaterials 72B(1):117-124.

Kim et al. "Controlled protein release from electrospun biodegradable fiber mesh composed of poly(e-caprolactone) and poly(ethylene oxide)" (Jun. 29, 2007) International Journal of Pharmaceutics 338 (1-2):276-283.

Kim et al. "Evaluations of Chitosan/Poly(D,L-lactic-co-glycolic acid) Composite Fibrous Scaffold for Tissue Engineering Application" 2013, Macromolecular Res. 21:931-939.

Kwon et al. "Electrospun nano- to microfiber fabrics made of biodegradable copolyesters: structural characteristics, mechanical properties and cell adhesion potential" (Jun. 2005) Biomaterials 26(18):3929-3939.

Lannutti et al. "Electrospinning for tissue engineering scaffolds" (Apr. 2007) Materials Science and Engineering: C 27(3):504-509.

Lee et al. "Biomedical Applications of Magnetically Functionalized Organic/Inorganic Hybrid Nanofibers" (2015) International Journal of Molecular Sciences 16:13661-13677.

Lee et al. "Characterization of nano-structured poly(e-caprolactone) nonwoven mats via electrospinning" (Feb. 2003) Polymer 44(4):1287-1294.

Lee et al. "Increased Mechanical Properties of Alligned and Isotropic Electrospun PVA Nanofiber Webs by Cellulose Nanowhisker Reinforcement" 2012, Macromolecular Research 20(1):76-83.

Li et al. "A three-dimensional nanofibrous scaffold for cartilage tissue engineering using human mesenchymal stem cells" (Feb. 2005) Biomaterials 26(6):599-609.

Li et al. "Biological response of chondrocytes cultured in three-dimensional nanofibrous poly(e-caprolactone) scaffolds" (Dec. 15, 2003) Journal of Biomedical Materials Research Part A 67A(4):1105-1114.

Li et al. "Electrospinning nanofibers as uniaxially aligned arrays and layer-by-layer stacked films" (Feb. 2004) Advanced Materials 16(4):361-366.

Li et al. "Multilineage differentiation of human mesenchymal stem cells in a three-dimensional nanofibrous scaffold" (Sep. 2005) Biomaterials 26(25):5158-5166.

Luu et al. "Development of a nanostructured DNA delivery scaffold via electrospinning of PLGA and PLGA and PLA-PEG block copolymers" (Apr. 29, 2003) Journal of Controlled Release 89(2):341-353.

Cheng et al. "Engineering the Microstructure of Electrospun Fibrous Scaffolds by Microtopography" 2013, BioMacromolecules 14:1349-1360.

Liu et al. "Electrospun Fibrous Mats on Lithographically Micropatterned Collectors to Control Cellular Behaviors" 2012, Langmuir 28:17134-17142.

*Nanofiber Solutions, LLC* v. *Acera Surgical, Inc.*, IPR2021-01016, Petition (PTAB May 28, 2021).

Chen et al. "Electrospun 3D Fibrous Scaffolds for Chronic Wound Repair" 2016, Materials 9(272):1-12.

Schneider et al. "Influence of pH on Wound-healing: a New Perspective for Wound-therapy" 2007 Arch. Dermatol. Res. 298:413-420.

Manavitehrani et al. "Biomedical Applications of Biodegradable Polyesters" 2016, Polymers 8(20):1-32.

Dhandayuthapani et al. "Polymeric Scaffolds in Tissue Engineering Application: A Review" 2011, International Journal of Polymer Science 2011, Article ID 290602, 19 pages.

Murthy et al. "Biodegradation of Polymers" 2012, Polymer Science: A Comprehensive Reference, 9:547-560.

Killeen et al. "Rapid Communication: Fully Synthetic Bioengineered Nanomedical Scaffold in Chronic Neuropathic Foot Ulcers" Oct. 2018, Wounds 30(10):E98-E101.

\* cited by examiner

BIOCOMPATIBLE FIBER TEXTILES FOR IMPLANTATION

CLAIM OF PRIORITY

This application is a continuation of U.S. application Ser. No. 14/216,976, entitled "Biocompatible Fiber Textiles for Implantation," filed Mar. 17, 2014, which claims benefit of and priority to U.S. Provisional Application No. 61/798,265, entitled "Biocompatible Fiber Textiles for Implantation," filed Mar. 15, 2013, each of which is incorporated by reference herein in its entirety.

BACKGROUND

In order to repair or replace organs in patients, two independent and often mutually exclusive parameters must be met. First, any implant must have structural integrity including a certain amount of rigidity to remain in place once implanted. Second, an implant must be biocompatible so that it is not rejected by the body or create damaging inflammation. In certain instances the attachment, penetration, and proliferation of cells is also required for an implant to function as an organ as opposed to a simple prosthesis. No prior implant has been able to embody such parameters. For example, decellularized organ scaffolds, gels, and polymer matrices have been implanted, but one or more mechanical or biological issues have arisen. As such, none of these systems have been able to provide the appropriate mechanical properties along with the necessary bio-compatibility.

SUMMARY

In an embodiment, a biocompatible textile may include at least one electrospun fiber, composed of at least one polymer, that is disposed on a mandrel, in which the electrospun fiber forms a plurality of windings on the mandrel, each winding of the plurality of windings forming an opening with an adjacent winding, thereby forming a plurality of openings between a plurality of adjacent windings. The plurality of openings may compose a mesh size.

In an embodiment, a biocompatible textile may include an at least one electrospun fiber, composed of at least one polymer, that is disposed longitudinally along a linear axis of a mandrel, thereby forming a plurality of textile threads, in which the at least one electrospun fiber forms openings between adjacent linearly deposited textile threads of a mesh size. The plurality of openings may compose a mesh size.

In an embodiment, a method for fabricating a biocompatible textile may include electrospinning a biocompatible polymer into an electrospun fiber, contacting the electrospun fiber with a particulate material having a solubility in a solvent, contacting the electrospun fiber with a receiving surface, thereby forming a polymer network thereon composed of a plurality of electrospun fiber threads and a plurality of spaces between adjacent electrospun fiber threads, removing the polymer network from the receiving surface, thereby forming a biocompatible textile, and contacting the biocompatible textile with the solvent thereby removing the particulate material. The plurality of openings may compose a mesh size.

In an embodiment, a replacement for an animal organ may include a biocompatible textile composed of at least one electrospun fiber, comprising at least one polymer, disposed on a mandrel, in which the electrospun fiber forms a plurality of windings on the mandrel, each winding of the plurality of windings forming an opening with an adjacent winding, thereby forming a plurality of openings between a plurality of adjacent windings, and the plurality of openings comprises a mesh size. Additionally, the mandrel may have a shape of the animal organ or part thereof, and at least one surface of the biocompatible textile comprises windings of the at least one electrospun fiber treated with a surface treatment process.

DETAILED DESCRIPTION

In some embodiments, a textile of embodiments herein may have a luminal structure composed of multiple windings of one or more biocompatible fibers. The term "textile" is defined herein as a spun, woven, or otherwise fabricated material comprising fibers. In some embodiments, the fibers may be wound about a mandrel as threads are wound around a bobbin. In some embodiments, the fibers may be deposited, in an essentially parallel manner, along a linear dimension of a mandrel or other surface form. In some embodiments, winding the textile may use electro-spinning techniques.

"Pore size" is thus defined herein as being the diameter of introduced pores, pockets, voids, holes, spaces, etc. introduced in an unmeshed structure such as block polymer, polymer sheet, or formed polymer scaffold and is specifically distinguished from "mesh size" as disclosed herein.

As used herein, the term "mesh size" is the number of openings in a textile per linear measure. For example, if the textile has 1200 openings per linear millimeter, the textile is defined 1200 mesh (e.g., sufficient to allow a 12 micron red blood cell to pass), which is easily convertible between imperial and metric units. A mesh size may be determined based on the number of fibers having a specified average diameter and an average opening size between adjacent fibers along a specified linear dimension. Thus, a textile composed of 10 µm average diameter fibers having 10 µm average diameter openings between adjacent fibers may have about 50 total openings along a 1 mm length and may therefore be defined as a 50 mesh textile.

As used herein, the term "implant" may refer to any structure that may be introduced for a permanent or semi-permanent period of time into a body. An implant may have the shape and size of a native organ or tissue that it may serve to replace. Alternatively, an implant may have a shape not related to a specific bodily organ or tissue. In yet another embodiment, an implant may have a shape of an entire bodily organ or tissue, or only a portion thereof. In still another example, an implant may be shaped like a portion of a bodily organ or tissue, or may simply comprise a patch of material. The implant may be designed for introduction into a body of an animal, including a human.

Disclosed herein are compositions and methods for use of textiles comprising spun fibers in biocompatible implants for patients. In certain embodiments, a polymer fiber is used such as polyurethane and/or polyethylene terephthalate. In some embodiments, a polymer fiber is spun over a mandrel so as to form a textile roll or tube. In some embodiments, the thickness of the textile roll or tube may be regulated by changing the number of rotations of the mandrel over time while the textile roll or tube collects the fiber. In certain other embodiments, the biocompatible textile has a mesh size of about 1 opening per mm to about 20 openings per mm Some non-limiting examples of mesh sizes may include about 1 opening per mm, about 2 opening per mm, about 4 opening per mm, about 6 opening per mm, about 8 opening per mm, about 10 opening per mm, about 15 opening per mm, about 20 opening per mm, or ranges between any two of these values (including endpoints). In some embodiments, the mesh size of the spun textile may be about 20 openings per mm to about 500 openings per mm Some non-limiting examples of mesh sizes may include about 20 openings per mm, about 40 openings per mm, about 60 openings per mm, about 80 openings per mm, about 100 openings per mm, about 200 openings per mm, about 300 openings per mm, about 400 openings per mm, about 500 openings per mm, or ranges between any two of these values (including endpoints). In other embodiments, the mesh size may be about 500 openings per mm to about 1000 openings per mm Some non-limiting examples of mesh sizes may include about 500 openings per mm, about 600 openings per mm, about 700 openings per mm, about 800 openings per mm, about 1000 openings per mm, or ranges between any two of these values (including endpoints). In some embodiments, the mesh size of the textile may be regulated by changing the speed and direction by which the fiber is deposited onto the mandrel, such as by example moving the position and direction in which the thread is spun onto the textile roll or tube.

The textile having a mesh size may not only provide lightweight and flexible mechanical support, but also in certain embodiments, may allow cells to migrate into and throughout the mesh over time and may improve the biocompatibility of the implant. In yet other embodiments, the textile may provide sufficient structural rigidity so as to be surgically secured into an implant site while retaining sufficient flexibility under load stresses such as compression, shear, and torsion so as to allow the patient to physically move about once the implant is in place.

In yet other embodiments, the textile may include an additional surface treatment of the polymer fiber which can be used to modulate and enhance cellular attachment to the fibers. In yet other embodiments, the textile may not cause untreatable inflammation or rejection when implanted in a patient. As such, in certain embodiments, the textile implant may not be subject to rejection or life-threating inflammation within 1 day, 3 days, 5 days, 7 days, 2 weeks, 3 weeks, a month or longer after implantation. In some embodiments, the textile implant can be retained in the patient for at least 1 day, 3 days, 5 days, 7 days, 2 weeks, 3 weeks, a month or longer. In certain embodiments, the implant may be retained in the patient for 6 months, a year, a term of years, or the lifetime of the patient. In some of the disclosed embodiments, spaces may be introduced through directional application of a polymer thread to a mandrel or other surface form during the electrospinning process as described herein. In some other embodiment, spaces may be introduced through the addition of particulates to the textile as the polymer fiber is deposited on a mandrel or other surface form during the electrospinning process as described herein.

While it is contemplated that any method or composition consistent with the disclosure is embodied, electrospun textiles may have specific advantages that are useful for implants. For example, when an electrospun textile is formed from a polymer network deposed on a mandrel, the traditional molding processed can be bypassed since the polymer already exists in the form of a thread before the implant is shaped. As such, a textile based approach to creating biocompatible implants allows control of four critical parameters that cannot be controlled using inherently combined polymerization and molding processes. First, since the polymer is formed as a thread as part of the electospinning process, there is no need for setting, curing or other time-consuming process. Second, the polymer fiber itself can be directed to any orientation for mesh spacing without resorting to chemical processes. The formation of a mesh obviates the need to create pores in an otherwise solid form. Third, the mesh size itself can be adjusted to be larger or smaller to promote ingrowth and proliferation of cells. Where such meshes are used to provide structural support for growing and migrating cells, the mesh may also operate as a cellular scaffold in addition to conferring the other advantages disclosed herein. In certain embodiments, a particle size can similarly be identified by the size of the mesh opening such as with the US sieve size, Tyler equivalent, mm, or inches. Fourth, the mesh can be sized to provide structural integrity such as rebound from deformation, and flexibility under load, and other advantageous mechanical properties.

Spinning Textiles

The biocompatible textiles disclosed herein may be manufactured by any method. One non-limiting method may include break or open-end spinning, in which slivers are blown by air onto a rotating drum where they attach themselves to the tail of a formed textile (such as thread, rope or yarn) that is continually being drawn out from the drum. Other non-limiting methods may include ring spinning and mule spinning. In certain embodiments, a spinning machine may take a roving, thin it and twist it, thereby creating a yarn which may be wound onto a bobbin.

In mule spinning, the roving is pulled off a bobbin and fed through rollers, which feed at several different speeds, thinning the roving at a consistent rate. The thread, rope or yarn is twisted through the spinning of the bobbin as the carriage moves out, and is rolled onto a cop as the carriage returns. Mule spinning produces a finer thread than ring spinning. The mule process is an intermittent process, because the frame advances and returns a specific distance, which can produce a softer, less twisted thread favored for fines and for weft. The ring process is a continuous process, the yarn being coarser, and having a greater twist thereby being stronger and better suited to be warped. Similar methods have various improvements such as a flyer and bobbin and cap spinning Electrospinning Textiles Electrospinning is a method of spinning a polymer fiber or polymer nanofiber from a polymer solution by applying of a high voltage potential between the polymer solution (or polymer injection system containing the polymer solution) and a receiving surface for the electrospun polymer nanofibers. The voltage potential may include voltages less than or equal to about 30 kV. The polymer may be ejected by a polymer injection system at a flow rate of less than or equal to about 50 ml/h. As the polymer solution travels from the polymer injection system toward the receiving surface, it may be elongated into sub-micron diameter electrospun polymer nanofibers typically in the range of, about 0.1 μm to about 100 μm. Some non-limiting examples of electrospun polymer nanofiber diameters may include about 0.1 μm, about 0.2 μm, about 0.5 μm, about 1 μm, about 2 μm, about 5 m, about 10 μm, about 20 μm, about 50 μm, about 100 μm, or ranges between any two of these values (including endpoints).

A polymer injection system may include any system configured to eject some amount of a polymer solution into an atmosphere to permit a flow of the polymer solution from the injection system to the receiving surface. In some non-limiting examples, the injection system may deliver a continuous stream of a polymer solution to be formed into a polymer nanofiber. In alternative examples, the injection system may be configured to deliver intermittent streams of a polymer to be formed into multiple polymer nanofibers. In one embodiment, the injection system may include a syringe under manual or automated control. In another embodiment, the injection system may include multiple syringes under individual or combined manual or automated control. In some examples, a multi-syringe injection system may include multiple syringes, each syringe containing the same polymer solution. In alternative examples, a multi-syringe injection system may include multiple syringes, each syringe containing a different polymer solution.

The receiving surface may move with respect to the polymer injection system or the polymer injection system may move with respect to the receiving surface. In some embodiments, the receiving surface may move with respect to the polymer injection system under manual control. In other embodiments, the surface may move with respect to the polymer system under automated control. In such embodiments, the receiving surface may be in contact with or mounted upon a support structure that may be moved using one or more motors or motion control systems. In some non-limiting examples, the surface may be a roughly cylindrical surface configured to rotate about a long axis of the surface. In some other non-limiting examples, the surface may be a flat surface that rotates about an axis approximately coaxial with the polymer fiber ejected by the polymer injection system. In yet some other non-limiting examples, the surface may be translated in one or more of a vertical direction and a horizontal direction with respect to the polymer nanofiber ejected by the polymer injection system. It may be further recognized that the receiving surface of the polymer nanofiber may move in any one direction or combination of directions with respect to the polymer nanofiber ejected by the polymer injection system. The pattern of the electrospun polymer nanofiber deposited on the receiving surface may depend upon the one or more motions of the receiving surface with respect to the polymer injection system. In one non-limiting example, a roughly cylindrical receiving surface, having a rotation rate about its long axis that is faster than a translation rate along a linear axis, may result in a roughly helical deposition of an electrospun polymer fiber forming windings about the receiving surface. In an alternative example, a receiving surface having a translation rate along a linear axis that is faster than a rotation rate about a rotational axis, may result in a roughly linear deposition of an electrospun polymer fiber along a liner extent of the receiving surface.

In some embodiments, the receiving surface may be coated with a non-stick material, such as, for example, aluminum foil, a stainless steel coating, polytetrafluoroethylene, or combination thereof, before the application of the electrospun polymer nanofibers. The receiving surface, such as a mandrel, may be fabricated from aluminum, stainless steel, polytetrafluoroethylene, or combination thereof to provide a non-stick surface on which the electrospun nanofibers may be deposited. In other embodiments, the receiving surface may be coated with a simulated cartilage or other supportive tissue. In some non-limiting examples, the receiving surface may be composed of a planar surface, a circular surface, an irregular surface, and a roughly cylindrical surface. One embodiment of a roughly cylindrical surface may be a mandrel. A mandrel may take the form of a simple cylinder, or may have more complex geometries. In some non-limiting examples, the mandrel may take the form of a hollow bodily tissue or organ. Non-limiting embodiments of such bodily tissues may include a trachea, one or more bronchii, an esophagus, an intestine, a bowel, a ureter, a urethra, a blood vessel, or a nerve sheath (including the epineurium or perineurium).

The polymer solution may be a fluid composed of a solid polymer liquid by the application of heat. Alternatively, the polymer solution can comprise any polymer or combination of polymers dissolved in a solvent or combination of solvents. The concentration range of polymer or polymers in solvent or solvents may be, without limitation, about 5 wt % to about 50 wt %. Some non-limiting examples of polymer concentration in solution may include about 5 wt %, about 10 wt %, about 15 wt %, about 20 wt %, about 25 wt %, about 30 wt %, about 35 wt %, about 40 wt %, about 45 wt %, about 50 wt %, or ranges between any two of these values (including endpoints).

Polymers

In accordance with embodiments herein, a polymer solution used for electrospinning may typically include synthetic or semi-synthetic polymers such as, without limitation, a polyethylene terephthalate, a polyester, a polymethylmethacrylate, polyacrylonitrile, a silicone, a polyurethane, a polycarbonate, a polyether ketone ketone, a polyether ether ketone, a polyether imide, a polyamide, a polystyrene, a polyether sulfone, a polysulfone, a polycaprolactone (PCL), a polylactic acid (PLA), a polyglycolic acid (PGA), a polyglycerol sebacic, a polydiol citrate, a polyhydroxy butyrate, a polyether amide, a polydiaxanone, and combinations or derivatives thereof. Alternative polymer solutions used for electrospinning may include natural polymers such as fibronectin, collagen, gelatin, hyaluronic acid, chitosan, or combinations thereof. It may be understood that electrospinning solutions may also include a combination of synthetic polymers and naturally occurring polymers in any combination or compositional ratio. In some non-limiting examples, the polymer solution may comprise a weight percent ratio of polyethylene terephthalate to polyurethane of about 10% to about 75%. Non-limiting examples of such weight percent ratios may include 10%, 25%, 33%, 50%, 66%, 75%, or ranges between any two of these values.

The type of polymer in the polymer solution may determine the characteristics of the biocompatible textile. Some textiles may be composed of polymers that are bio-stable and not absorbable or biodegradable when implanted. Such textiles may remain generally chemically unchanged for the length of time in which they remain implanted. Alternative textiles may be composed of polymers that may be absorbed or bio-degraded over time. Such textiles may act as an initial template for the repair or replacement of organs and/or tissues. These organ or tissue templates may degrade in situ once the tissue or organs have been replaced or repaired by natural structures and cells. It may be further understood, that a biocompatible textile may be composed of more than one type of polymer, and that each polymer therein may have a specific characteristic, such as stability or biodegradability.

Polymer solutions may also include one or more solvents such as acetone, dimethylformamide, dimethylsulfoxide, N-methylpyrrolidone, acetonitrile, hexanes, ether, dioxane, ethyl acetate, pyridine, toluene, xylene, tetrahydrofuran, trifluoroacetic acid, hexafluoroisopropanol, acetic acid, dimethylacetamide, chloroform, dichloromethane, water, alcohols, ionic compounds, or combinations thereof.

The polymer solutions may also include additional materials. Non-limiting examples of such additional materials may include radiation opaque materials, antibiotics, growth factors, vitamins, cytokines, steroids, anti-inflammatory drugs, small molecules, sugars, salts, peptides, proteins, cell factors, DNA, RNA, or any combination thereof.

Incorporation of an Anti-Static Bar

During electrospinning, polymer nanofibers are driven toward a receiving surface by charge separation caused by an applied voltage. The receiving surface typically is a conductive surface, composed of, for example, aluminum or copper. In some embodiments, the receiving surface is covered by a thin layer of plastic, ranging, for example, between about 0.001 inches (about 0.025 mm) to about 0.1 inches (about 2.5 mm) thick. The force that drives the electrospun polymer solution from the polymer injection system toward the receiving surface is derived from mobile ions within the polymer solution or melt. The polymer solution ejected by the polymer injection system may have a net positive or negative charge, depending upon the polarity of the voltage applied to the polymer injections system and the receiving surface. When the electrospun polymer nanofiber is deposited on the collector surface to form polymer nanofiber threads, a charge will build up as subsequent nanofiber thread layers are collected. It is believed that as the charge builds up on the receiving surface, the nanofibers threads, having a similar charge, will be repelled. This electrostatic repelling force may, thus, lead to irregularly arranged nanofiber threads that will have a lower degree of alignment. In order to reduce the effects of surface charge on the receiving surface or its polymer nanofiber threads, the use of an anti-static device, such as a bar, may be incorporated into the process to improve nanofibe thread alignment. The anti-static bar bombards the receiving surface with positively or negatively charged ions in the form of, for example, a plasma or corona discharge thereby neutralizing the charge on the receiving surface. Therefore, as fiber builds up over the receiving surface, successive layers of nanofiber threads will deposit more uniformly in a side-by-side arrangement (parallel relationship) to increase the alignment. In one embodiment, the position of an anti-static bar is parallel to the surface of the receiving surface, (for example, a roughly cylindrical mandrel, wheel, device, or plate) and may be, for example, about 0.5 inches (about 13 mm) to about 3 inches (about 75 mm) away from the receiving surface.

Experimental results demonstrated that nanofiber thread alignment on the receiving surface was improved significantly with the addition of an anti-static bar, when compared to samples spun under the same conditions without the anti-static bar. For example, the alignment of nanofiber threads can be about 83% at a low angle orientation when deposited on a receiving surface lacking an anti-static bar. However, a 12% increase in fiber alignment—to about 95%—may be observed with the use of an anti-static bar. The use of an anti-static bar may also lead to improvements in nanofiber thread alignment on the receiving surface for processes incorporating polymer injection systems having multiple syringes. When nanofiber threads are deposited on a receiving surface lacking an anti-static bar, the nanofiber thread alignment can be low, with about 74% of nanofiber threads deposited in a low angle orientation. With an anti-static bar, under the same spinning conditions, the alignment can become about 92%. It may be appreciated that additional embodiments may include processes that incorporate the use of more than one anti-static bar.

Combined High Velocity and Alternating Ground Alignment

Enhanced alignment of polymer nanofibers produced during electrospinning has been achieved by various methods including, for example, high velocity fiber collection (for example, on a receiving surface, such as a mandrel, rotating at a high velocity) and fiber collection between sequentially placed electrodes on the rotating receiving surface. In one non-limiting embodiment, the receiving surface may be the rim surface of a metal spoked wheel. The rim surface of the wheel may be coated with a thin insulating layer, such as, for example, a thin layer of polystyrene or polystyrene film. In one non-limiting example, the sequential electrodes may be fabricated from conductive tape placed widthwise across the insulating material. At least one end of each tape electrode may contact one or more metal wheel spokes. The conductive tape may be composed of, for example, carbon or copper and may have a width of about 0.1 inches (0.25 cm) to about 2 inches (about 5 cm). In some embodiments, the conductive tape may be spaced in uniform intervals around the wheel rim. The intervals between the conductive tape and the insulating surface may create alternating layers of conductive and non-conductive surfaces. The metal spokes may be in electrical contact with the source of the electrospinning voltage providing the voltage difference between the polymer injection system and the receiving surface. The combination of a high speed rotational surface and a multiply grounded electrical surface may lead to enhanced fiber alignment.

Figure 1:
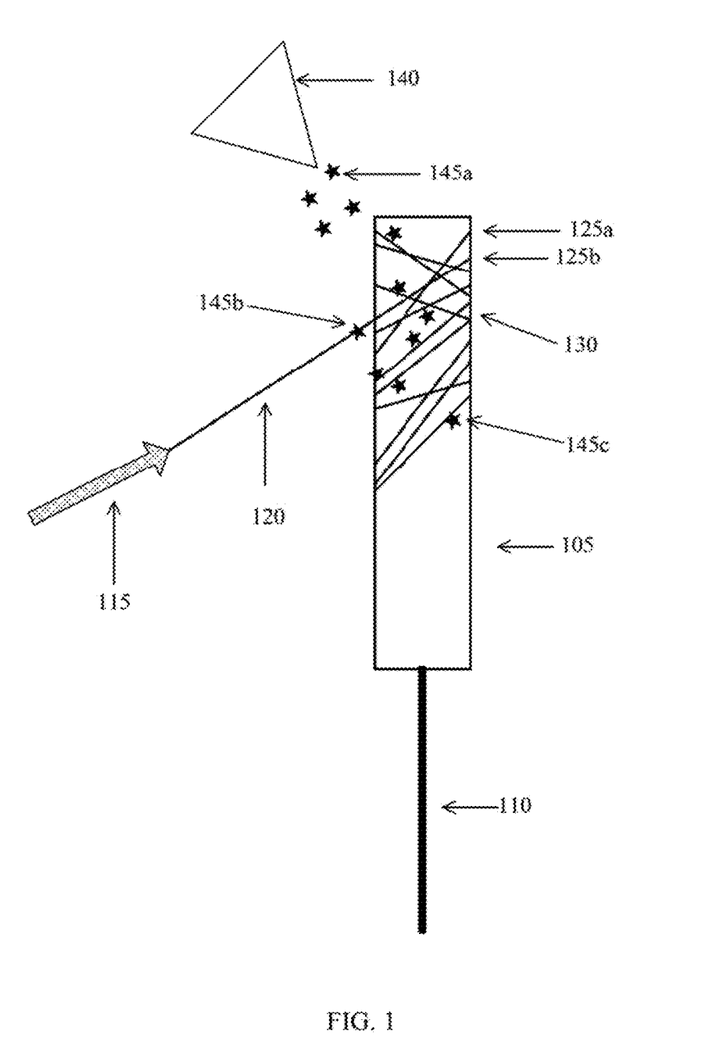
FIG. 1 illustrates an embodiment of a system for electrospinning a polymer fiber onto a mandrel in accordance with the present disclosure.

FIG. 1 illustrates one example of a system for electrospinning a polymer nanofiber onto a mandrel to form a polymer network. A polymer injection device 115 may express the polymer solution in drops or in a continuous stream. An electrospun polymer nanofiber 120 may form during the transit of the liquid polymer from the injector 115 to the mandrel 105. A voltage source may provide a high voltage to the injection device 115 with an appropriate ground to the mandrel 105. The mandrel 105 may be mounted on a movable support 110. In one non-limiting embodiment, the high voltage ground may be in electrical communication with the support 110. In another non-limiting embodiment, the high voltage ground may be in electrical communication with the mandrel 105.

In one non-limiting example, the support 110 may cause the mandrel 105 to rotate either in a single direction during the electrospinning process, or in alternating directions. In an alternative non-limiting example, the support 110 may cause the mandrel 105 to translate along one or more linear axes, x, y and/or z during the electrospinning process, or in alternating directions. Such linear motions may permit the fiber 120 to attach to any portion along the length of the mandrel 105 (viz. in the z-direction). Alternatively, liner motions may cause the mandrel 105 to vary in its distance from the tip of the injection device 115 (x- and/or y-directions). It may be understood that the support 110 may move the mandrel 105 in a complex motion including both rotational and translational motions during the electrospinning process. It may further be appreciated that the speed of rotation and/or translation of the mandrel 105 during the electrospinning process may be uniform or non-uniform. It may also be appreciated that the mandrel 105 on the support 110 may be static and that the injection device 115 may rotate and/or translate with respect to the static mandrel.

As illustrated in FIG. 1, the electrospun fiber 120 may be wound about the mandrel 105 in a manner similar to that used to wind spun thread on a bobbin. The fiber 120 may be wound in any number of controlled configurations about the mandrel 105 based, at least in part, on one or more factors including the rate of polymer solution injection by the injection device 115, the voltage potential between the injection device and the mandrel, and the rotational and/or translation speed of the support 110. The mandrel 105 may have any shape appropriate to the type of luminal structure intended for manufacture. In one non-limiting example, the mandrel 105 may have a simple tubular shape, for example, for a vascular support structure. In another non-limiting example, the mandrel 105 may be composed of a structure having a single tubular end, and a bifurcated tubular end. It may be apparent that such a shape may be used to fabricate a polymer network appropriate to replace a trachea and attendant bronchi. In one non-limiting example, the mandrel 105 may be composed of metal. In another non-limiting example, the mandrel 105 may be coated with a non-stick material, such as, for example, aluminum foil or polytetrafluoroethylene, to permit easy removal of the polymer network from the mandrel. In still another non-limiting embodiment, the mandrel 105 may have a collapsible construction, so that the mandrel may be removed from the polymer network by collapsing the mandrel within the polymer network, thereby freeing the polymer network from the mandrel surface. In yet another non-limiting embodiment, the mandrel 105, having a completed polymer network wrapped around it, may be sprayed with a solvent, such as an alcohol, to loosen the polymer network from the mandrel, thereby permitting the polymer network to be removed from the mandrel, thereby forming the biocompatible textile. A mandrel 105 having a more complex shape may be fabricated from a number of reversibly attachable components. A polymer network fabricated on such a mandrel 105 may be removed from the mandrel surface by dissembling the mandrel.

As illustrated in FIG. 1, a rotating mandrel 105 may cause the fiber 120 to wrap around the mandrel outer surface forming a plurality of windings 125a,b. The windings 125a,b may be formed in regular, irregular, or a combination of regular and irregular patterns. In one embodiment, the windings 125a,b may form a regular right-handed helix. In one embodiment, the windings 125a,b may form a regular left-handed helix. In some embodiments, the windings 125a,b may form a helix with about the same spacing between adjacent windings. In some embodiments, the windings 125a,b may form a helix in which adjacent windings have different spacing between them. In some additional embodiments, the windings 125a,b may not form a regular helix, and there may be overlap among some number of windings. In still another embodiment, the windings 125a,b may be wound around the mandrel 105 in a random manner.

It may be apparent that the polymer network may be composed of a number of windings 125a,b. The polymer network may be composed of a single layer of windings 125a,b. In alternative embodiments, the polymer network may be composed of a number of layers of windings 125a,b. In some embodiments, a number individual fibers 120 may be wound consecutively around the mandrel 105 to form one or more layers. In alternative embodiments, each layer may be composed of a number of windings 125a,b of a single fiber 120. In still alternative embodiments, a number of layers may be composed of a single fiber 120, wound around the mandrel 105 in a succession of layers. It may be appreciated that a void or inter-fiber spacing 130 may be formed between adjacent windings, such as between winding 125a and 125b. Such inter-fiber spacings 130 may have a diameter of about 2 microns to about 5 microns. Alternatively, such inter-fiber spacings 130 may have a diameter of about 30 micron to about 50 microns. It may be apparent that a textile may include a plurality of inter-fiber spacings 130 having a diameter of about 2 microns to about 50 microns. Non-limiting examples of such inter-fiber spacings may include about 2 µm, about 4 µm, about 6 µm, about 8 µm, about 10 µm, about 20 µm, about 30 µm, about 40 µm, about 50 µm, or ranges between any two of these values (including endpoints). In additional non-limiting examples, the inter-fiber spacings 130 may have a diameter less than or about equal to about 200 microns. The textile may alternatively be characterized by a mesh size. In some non-limiting embodiments, the textile may have a mesh size of about 20 inter-fiber spacings 130 per mm to about 500 inter-fiber spacings 130 per mm Non-limiting examples of such mesh sizes may include about 20 spacings per mm, about 40 spacings per mm, about 60 spacings per mm, about 80 spacings per mm, about 100 spacings per mm, about 200 spacings per mm, about 300 spacings per mm, about 400 spacings per mm, about 500 spacings per mm, or ranges between any two of these values (including endpoints).

An alternative method for fabricating a biocompatible polymer textile may include surface treatments to further adjust the mesh size of the polymer network. In one embodiment, a surface treatment may include contacting particulate material 145a with one or more of the electrospun fiber 120, the mandrel 105, or the polymer network disposed on the mandrel. In one non-limiting method, a particulate material 145b may be contacted with the electrospun fiber 120 during the spinning step (145b) before the electrospun nanofiber contacts the mandrel 105. In an alternative method, the particulate material 145c may be contacted with a polymer network of electrospun fibers (145c) in contact with the mandrel 105. The particulate material 145a may be supplied from a particulate source 140 placed above or otherwise proximate to the electrospun fiber 120 or mandrel 105. The particulate source 140 may include any device known in the art including, without limitation, a sieve or a shaker. The particulate source 140 may be mechanical in nature and may be controlled by an operator directly, a mechanical controller, an electrical controller, or any combination thereof.

The particulate material 145a may be chosen from any material capable of being dissolved in a solvent that may not otherwise dissolve the electrospun fibers. In one non-limiting example, the solvent may be water, and the particulate material 145a may include water soluble particulates. Non-limiting embodiments of such water-soluble particulates may include a water soluble salt, a water soluble sugar, a hydrogel, or combinations thereof. Non-limiting examples of a water soluble salt may include NaCl, CaCl, $CaSO_4$, or KCl. Non-limiting examples of water soluble sugars may include sucrose, glucose, or lactose. The particulate material 145a may have an average size of about 5 µm to about 300 µm. Non-limiting examples of the average size of such particulate material 145a may include about 5 µm, about 10 µm, about 20 µm, about 40 µm, about 60 µm, about 80 µm, about 100 µm, about 150 µm, about 200 µm, about 250 µm, about 300 µm, or ranges between any two of these values (including endpoints).

Fabrication methods of multi-layer textiles may include additional steps. In some examples, groups of layers may be tack welded together either chemically or thermally. Alternatively, layers may be sintered together either through thermal or chemical means.

As disclosed above, a textile may be composed of a number of layers of windings 225. Additional features may be added to the textile. In some non-limiting embodiments, the textile may include one or more curved support structures. Such structures may include rings or U-shaped supports disposed on the interior of the textile, exterior of the textile, or between successive layers of fiber windings 125a,b. The curved supports may have any dimensions appropriate for their use. In some non-limiting examples, the supports may have a width of about 0.2 mm to about 3 mm. In some other non-limiting examples, the supports may have a thickness of about 1 mm to about 5 mm. Such supports may be composed of one or more of the following: metals, ceramics, and polymers. Non-limiting examples of polymers used in such curved supports may include: a polyethylene terephthalate, a polyester, a polymethylmethacrylate, polyacrylonitrile, a silicone, a polyurethane, a polycarbonate, a polyether ketone ketone, a polyether ether ketone, a polyether imide, a polyamide, a polystyrene, a polyether sulfone, a polysulfone, a polycaprolactone (PCL), a polylactic acid (PLA), a polyglycolic acid (PGA), a polyglycerol sebacic, a polydiol citrate, a polyhydroxy butyrate, a polyether amide, a polydiaxanone, a chitosan, and combinations or derivatives thereof. Such support may further be composed of materials that may be non-resorbable or fully degradable. Such supports may be affixed on the mandrel 105 before the fiber 120 is wound about the mandrel surface to form the polymer network. Alternatively, such supports may be affixed on one pre-wound layer of fiber 120 of the polymer network before additional layers are wound on top of it. In yet another embodiment, such supports may be attached to the outer surface of the polymer network after the winding process is complete but before the polymer network is removed from the mandrel 105. Alternatively, after the polymer network has been removed from the mandrel 105, thereby forming the biocompatible textile, additional supports may be added. Supports may be affixed on the polymer network or textile by any appropriate means, including, but not limited to, gluing, heat welding, and solvent welding. Additional supports may be formed of a mesh material over which the fibers 120 may be spun. Such a mesh support my be rigid, collapsible, and/or expandable.

The polymer network may receive any of number of additional surface treatments while still in contact with the receiving surface. Alternatively, once the polymer network has been removed from the receiving surface, thereby forming the implantable biocompatible textile, such surface treatments may also be applied. Non-limiting examples of such surface treatments may include, without limitation, washing in a solvent, drying with a gas stream, sterilizing, sintering, or treating with a plasma discharge. Washing solvents may include water and alcohol. A drying gas stream may include air, nitrogen, or inert gas such as argon. A gas stream may include pressurized air or pressurized ionized air. Sterilization techniques may include gamma irradiation. Plasma discharge treatments may be performed in air or in another gas such as carbon tetrafluoride.

The disclosure above includes a number of embodiments and examples of polymer networks and biocompatible textiles fabricated by electrospinning a polymer to form windings about a mandrel. Such windings may be fabricated by rotating the mandrel about a longitudinal axis and contacting the eletrospun polymer nanofiber with the mandrel. During the winding process, the mandrel additionally may be translated in any of a number of directions (in an x-direction, a y-direction, and a z-direction) with respect to the polymer injection device while simultaneously rotating about its longitudinal axis. Alternatively, the polymer networks or biocompatible textiles may be fabricated by translating the mandrel along a longitudinal axis to receive the electrospun polymer and rotating after a translation step has been accomplished. The resulting polymer network structure may not include windings (that is, a fiber deposited on the mandrel in a circular or curved path about the mandrel longitudinal axis) but rather may be composed of overlaid linear threads of fibers deposited on the mandrel surface along the longitudinal axis of the mandrel.

Figure 2A:
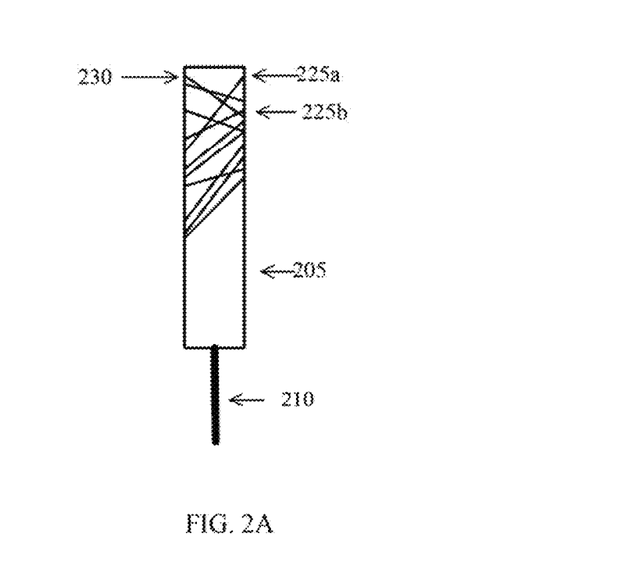
FIG. 2A illustrates an embodiment of a system for forming electrospun fibers as windings on a mandrel surface in accordance with the present disclosure.
Figure 2B:
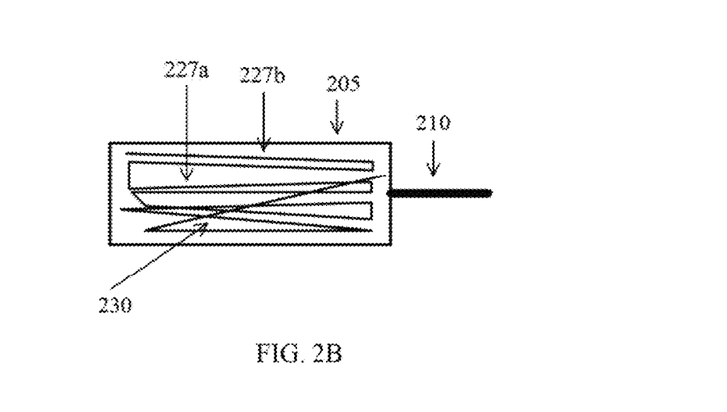
FIG. 2B illustrates an embodiment of a system for forming electrospun fibers as threads along the longitudinal axis of a mandrel in accordance with the present disclosure.

FIGS. 2A and 2B illustrate some examples of these geometries. As illustrated in FIG. 2A, mandrel 205 on a support 210 may rotate about the longitudinal axis of the mandrel. The electrospun polymer may be contacted with the mandrel 205 while the mandrel rotates, thereby producing windings 225a, 225b about the longitudinal axis of the mandrel with a spacing 230 therebetween. As illustrated in FIG. 2B, the mandrel 205 on the support 210 may be linearly translated while the polymer nanofiber contacts the mandrel surface. As a result, the electrospun nanofibers may form one or more textile threads 227a,b having a primarily longitudinal orientation along the mandrel longitudinal axis. These textile threads 227a,b may also be characterized by an inter-fiber spacing 230. It may be appreciated that polymer networks or biocompatible textiles having a variety of fiber and/or winding orientations and spaces may be fabricated based on the direction and orientation of mandrel motion with respect to the polymer injector.

It may be understood that in the above disclosure, the use of a mandrel as a polymer receiving surface is not considered limiting. Other types of surfaces, including planar surfaces, circular surfaces, and irregular surfaces, may equally be used as receiving surfaces for the polymer electrospun fibers. Rotational and translations motions of such alternative receiving surfaces may result in any type of orientation of polymer nanofiber threads on or about the receiving surface. Thus, such polymer nanofiber threads may form, without limitation, windings, linear alignments, star-shaped alignments, or random alignments.

Biocompatibility

In certain instances, textiles can be manufactured that lack openings between the fibers, and may be considered "meshless" textiles. In such "meshless" textiles, the fibers may be too big to allow openings between neighboring fibers. Such fibers in "meshless" textiles may almost entirely overlap each other, thereby creating an effectively continuous textile surface. Pores, including, without limitation, pockets, spaces, voids, and holes, may be introduced into such "meshless" textiles. Those having skill in the art may recognize that, as one non-limiting example, methods capable of incorporating pores into a polymer block may also be used to introduce pores into "meshless" textiles. An artisan having average skill in the art may recognize that techniques used for introducing pores into a construct fabricated from a polymer may include, without limitation, solution casting, emulsion casting, polymer blending, and phase transition techniques.

Implants and methods that lead to patient death, or fail to delay, prevent, or mitigate morbidity and mortality, are not within the meaning of the term "biocompatible". As such, in some embodiments, ineffective, toxic, or deadly compositions are expressly disclaimed herein as they do not meet the necessary requirement of being biocompatible. In some embodiments, non-biocompatible compositions that are specifically disclaimed are: molded nanocomposites, molded polylactic acid (PLA), molded polyglycolic acid (PGA), molded polycaprolactone (PCL), polycaprolactone/polycarbonate (80:20%) polyhedral oligomeric silsesquioxane; polyhedral oligomer silsesquioxane nanocages; molded protein materials, molded collagen; molded fibrin, molded polysaccharides molded chitosan, molded glycosaminoglycans (GAGs); molded hyaluronic acid, a set nanocomposite material composed of polyhedral oligomeric silsesquioxane (POSS) covalently bonded to poly(carbonate-urea)urethane (PCU) to form a nanocomposite "POSS-PCU" polymer; a POSS-PCU fluid; coagulated POSS-PCU fluid; a POSS-PCU polymer fluid comprising salt crystals; a coagulated POSS-PCU polymer wherein the salt crystals are dissolved after coagulation to form pores; a coagulated POSS-PCU polymer wherein the salt crystals are a sodium salt, a lithium salt, a potassium salt, carbonate or bicarbonate salt, calcium carbonate, cobalt(II) carbonate, copper(II) carbonate, lanthanum carbonate, lead carbonate, lithium carbonate, magnesium carbonate, manganese(II) carbonate, nickel(II) carbonate, potassium carbonate or sodium carbonate; a POSS-PCU polymer wherein the average pore diameter may is about 20-100 microns; a molded polymer wherein the average pore diameter is about 20-100 microns, from about 1 nm to about 500 microns, an average diameter of about 10 nm to about 1 micron, about 1 to about 10 microns, about 10 to about 100 microns, about 10 to about 50 microns, about 50 to about 100 microns, about 100 to about 200 microns, about 200 to about 500 microns, and about 50-100 microns; and a polymer fluid containing 50% sodium bicarbonate having an average crystal size of about 40 microns.

Surgical Procedures

While the prior disclosed composition of non-textile implants are not within the scope of the disclosure, certain other methods including surgical methods can be easily adapted for use with the disclosed textile implants. For example, a subject may be evaluated using one or more imaging techniques to identify the location and extent of damaged tissue that needs to be removed. In some non-limiting examples, the disclosed textiles may be seeded on both external and luminal surfaces with compatible cells that retain at least some ability to differentiate. In some embodiments, the cells may be autologous cells (e.g., mononuclear cells) that may be isolated from the patient (e.g., from the patient bone marrow) or a compatible donor. The seeding process may take place in a bioreactor (e.g., a rotating bioreactor) for a few days prior to surgery. Just prior to surgery, additional cells may be added to the luminal surface of a synthetic tissue composed of a biocompatible textile. In some embodiments, these cells may be epithelial cells, which may be isolated from the patient's airway if the tissue is an airway tissue. Additionally, one or more growth factors may be added to the synthetic tissue immediately prior to surgery. The biocompatible textile incorporating such cells and/or additional chemical factors may then be transplanted into the patient to replace the damaged tissue that has been removed. The patient may be monitored post-surgically for signs of rejection or of a poorly functional airway transplant. It should be appreciated that the addition of cells and/or chemical factors to the biocompatible textile may not be required for every transplant surgery. Any one or more of these procedures may be useful alone or in combination to assist in the preparation and/or transplantation of a synthetic organ or tissue.

In certain embodiments, the biocompatible textiles disclosed herein are used as a tracheal implant. The natural trachea is a cartilaginous and membranous tube that extends from the lower part of the larynx (at the level of the sixth cervical vertebra) to the upper border of the fifth thoracic veltebra, where it branches to form the two bronchi. The trachea has the shape of a cylinder that is flattened at the back (posterior). The front (anterior) is convex. Without intending to be bound, a typical adult human trachea is at least about 10 cm long, and about 2-2.5 cm wide. However, it is generally larger in males and smaller in females. Sometimes, because of disease or trauma, a patient would benefit from having support or replacement of their airway or portion thereof (e.g., a trachea or portion thereof, a bronchus or portion thereof, or a combination thereof) with a biocompatible textile.

Any airway implant, whether comprising molded implants or textile implants, may be shaped or formed to represent the region or regions of the airway that is being replaced. In some embodiments, the airway implant may be roughly cylindrical, thereby forming an air flow conduit after implantation. Alternatively, the air flow conduit can have the natural shape of an airway region. For example, in cross-section, the conduit may have a D shape with a convex anterior (e.g., U-shaped) and a relatively straight posterior. The length of the conduit can be designed to effectively match (or be slightly longer than) the length of the airway region being replaced. The air flow conduit can be modeled on the portion of the patient's tissue that is to be replaced by the implant. Accordingly, the dimensions and shape of the implant can be designed to match those of the airway region being replaced. It should be appreciated that, depending on the region that is being replaced, the overall shape of the conduit may be a straight conduit, a Y-shaped bifurcated conduit, or an L-shaped conduit.

As to care of a patient after implantation, certain biological functions may be monitored. For example, after implantation of a synthetic or natural trachea, patient follow-up may include, but is not limited to, endoscopic evaluation (flexible and/or rigid bronchoscopy) of the transplanted airway every day for the first week, every other day for the second week, once a month for the first six months thereafter, and every 6 months for the first 5 years thereafter. Additional patient follow-up may include an evaluation of the blood count, including white blood cell differentials, every second day for the first two weeks, evaluation of the hematopoietic stem cells, immunogenic evaluations (for example, a blood sample may be taken to study histocompatibility of the implant by evaluating the antibodies after 3 days, 7 days, 30 days, 3 months, 6 months, and 12 months after the transplant,), and computerized tomography of the neck and chest. Longer term patient follow-up for a transplanted airway can be performed at month 1, month 3, and month 6 of the follow-up, and every 6 months thereafter for the first 5 years. Additional oncological follow-up will be life-long and may include the standard evaluations for such medical condition. In certain embodiments, a biocompatible textile implant may be retained within the patient for 1 day, 3 days, 5 days, 7 days, 2 weeks, 3 weeks, or even a month or longer after implantation. Thus, such textiles can be retained in the patient for at least these lengths of time commensurate with biocompatibility of the implant as disclosed herein. In certain embodiments, a biocompatible textile implant is retained in a patient for 6 month, a year, a term of years, or even as long as the lifetime of the patient.

Although disclosed above are examples of the use of a biocompatible textile to replace tracheae or laryngeal structures, it may be appreciated that other biological structures, tissues, and organs having a luminal structure may also be replaced by biocompatible textile devices. Some non-limiting examples of such luminal structures may include a trachea, a trachea and at least a portion of at least one bronchus, a trachea and at least a portion of a larynx, a larynx, an esophagus, a large intestine, a small intestine, an upper bowel, a lower bowel, a vascular structure, and portions thereof.

In order to illustrate the various features disclosed above, the following non-limiting examples are provided.

EXAMPLES

Example 1

Method of Preparing a Biocompatible Textile

In preparing an exemplary textile, a polymer nanofiber precursor solution was prepared by dissolving 2-30 wt % polyethylene terephthalate (PET) in a mixture of 1,1,1,3,3,3-hexafluoroisopropanol and trifluoroacetic acid, and the solution was heated to 60° C. followed by continuous stirring to dissolve the PET. The solution was cooled to room temperature and the solution placed in a syringe with a blunt tip needle. The nanofibers were formed by electrospinning using a high voltage DC power supply set to 1 kV-40 kV positive or negative polarity, a 5-30 cm tip-to-substrate distance, and a 1 µl/hr to about 100 ml/hr flow rate from the syringe. It is possible to use a needle array of up to 1,000's of needles to increase output. An approximately 0.2-3.0 mm thickness of randomly oriented and/or highly-aligned fibers were deposited onto a receiving surface. Polymer rings were introduced onto the receiving surface and over the previously spun fibers, and an additional approximately 0.2-3.0 mm of fiber was added over the surface (including the additional polymer rings) while the form was rotated. The textile was placed in a vacuum overnight to ensure removal of residual solvent (typically less than 10 ppm) and treated using a radio frequency gas plasma for 1 minute to make the fibers more hydrophilic and promote cell attachment.

Example 2

A Biocompatible Textile Fabricated with Soluble Particulate Materials

Figure 3A:
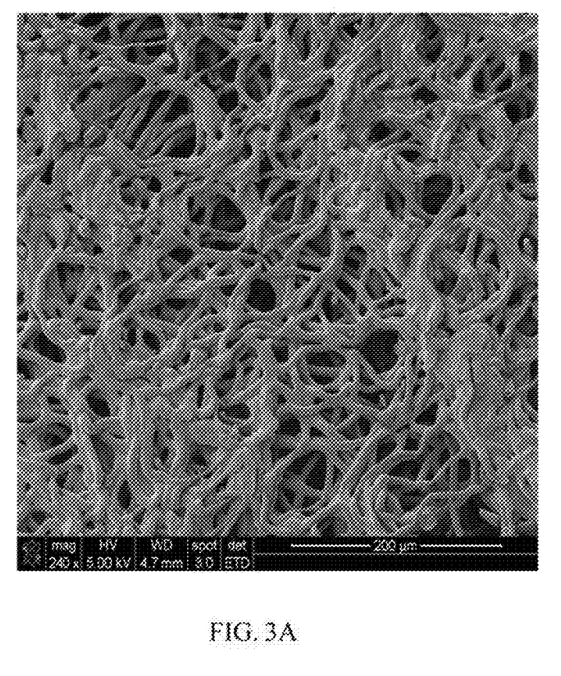
FIGS. 3A and 3B depict a biocompatible textile formed without the addition of a water soluble material and a biocompatible textile formed with the addition of a water soluble material, respectively, in accordance with the present disclosure.
Figure 3B:
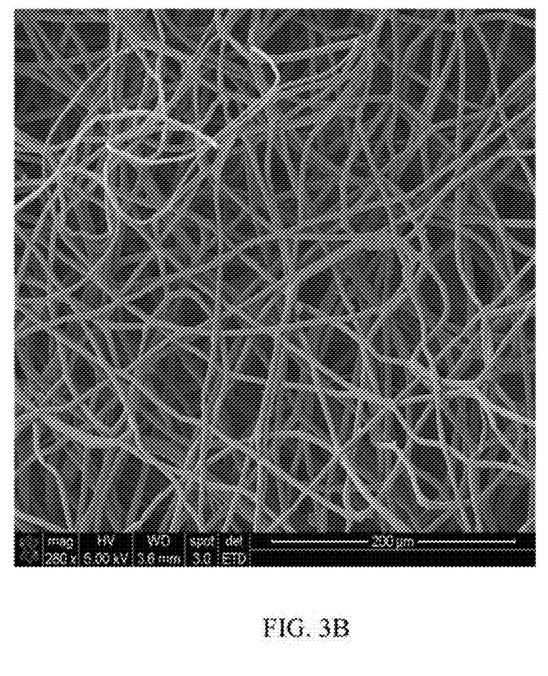

FIGS. 3A and 3B depict two micrographs of biocompatible textiles, one formed without the addition of a soluble particulate material (FIG. 3A) and one formed with the addition of the soluble particulate material (FIG. 3B). The textiles were formed from a solution of polydioaxone dissolved in hexafluoroisopropanol at a concentration of about 13 wt %. Polymer fibers having a fiber diameter of about 7 µm were electrospun onto a mandrel. FIG. 3A depicts the textile created from the polydioxanone electrospun alone onto the mandrel and demonstrates a porosity of about 60% (in which porosity may be defined as the fraction of void space in a material). It may be observed that the porosity appears inconsistent across the area depicted in FIG. 3A. A low porosity scaffold may be beneficial in applications where cellular infiltration is to be avoided or to decrease water permeability. However, a low porosity scaffold may be a disadvantage or a flaw in applications in which cellular infiltration in the scaffold may be desired. It may be appreciated that fibers bonded together as depicted in FIG. 3A may have mechanical properties that differ from those of a mesh scaffold lacking such bonding between fibers.

FIG. 3B illustrates a micrograph of a textile formed from the same polymer solution and solvent, but which further included small particulates of NaCl added to the fiber during winding, to form a polymer network including salt. The salt particles had an average size of about 50 µm. To remove the salt from the polymer network, the network was submerged in three successive changes of water under gentle agitation using a stir bar for about 24 hrs. It may be observed in FIG. 3B that the textile mesh is more regular, having an average porosity of about 90%. It may be appreciated that the addition of a soluble particulate material having a known size during the fabrication of the textile may produce a more homogeneous porosity and may also be a more reproducible process for fabricating the textiles. Reproducibility of textile properties may improve the utility of the textiles in that the textiles may be more readily fabricated to meet known specifications. In addition to improved reproducibility of the electrospinning process, the addition of soluble particulates can facilitate the customization of the mesh size for specific applications. In one non-limiting example, it may be necessary to increase the mesh size of the textile to accommodate the seeding or culturing of large clusters of cells presented to the textile as cell spheroids. Such spheroids may contain hundreds of cells and may be up to several hundred microns in diameter. The larger mesh size may allow these spheroids to fit into the scaffold without destroying the cell cluster.

While the present invention has been illustrated by the description of exemplary embodiments thereof, and while the embodiments have been described in certain detail, it is not the intention of the Applicants to restrict or in any way limit the scope of the appended claims to such detail. Additional advantages and modifications will readily appear to those skilled in the art. Therefore, the invention in its broader aspects is not limited to any of the specific details, representative devices and methods, and/or illustrative examples shown and described. Accordingly, departures may be made from such details without departing from the spirit or scope of the applicant's general inventive concept.

What is claimed is:

1. A biocompatible textile comprising:
a network of a plurality of windings formed into a luminal structure, the plurality of windings comprising at least one polymeric electrospun fiber;
wherein the at least one polymeric electrospun fiber comprises a combination of polyethylene terephthalate and polyurethane in a weight percent ratio of polyethylene terephthalate to polyurethane of 10% to 75%; and
wherein the network has a mesh size of 1 opening per mm to 20 openings per mm.

2. The biocompatible textile of claim 1, wherein the at least one polymeric electrospun fiber comprises an at least one surface-treated polymeric electrospun fiber.

3. The biocompatible textile of claim 1, wherein the plurality of windings forms a plurality of circumferential layers.

4. The biocompatible textile of claim 3, further comprising at least one curved polymer support in mechanical communication with at least one of the plurality of circumferential layers.

5. The biocompatible textile of claim 4, wherein the at least one curved polymer support is a U-shaped support.

6. The biocompatible textile of claim 1, shaped into a replica of an organ selected from the group consisting of a trachea, a trachea and at least a portion of at least one bronchus, a trachea and at least a portion of a larynx, a larynx, an esophagus, a large intestine, a small intestine, an upper bowel, a lower bowel, a vascular structure, and portions thereof.

7. A method for fabricating a biocompatible textile comprising:
   electrospinning a biocompatible polymer into an electrospun fiber, wherein the electrospun fiber comprises a combination of polyethylene terephthalate and polyurethane in a weight percent ratio of polyethylene terephthalate to polyurethane of 10% to 75%;
   contacting the electrospun fiber with a particulate material having a solubility in a solvent;
   contacting the electrospun fiber with a mandrel, thereby forming a polymer network thereon comprising a plurality of windings formed into a luminal structure, the plurality of windings comprising a plurality of electrospun fiber threads having a plurality of spaces between adjacent electrospun fiber threads;
   removing the polymer network from the mandrel; and
   dissolving the particulate material with the solvent that may not otherwise dissolve the electrospun fibers, thereby forming a biocompatible textile having a mesh size of 1 opening per mm to 20 openings per mm.

8. The method of claim 7, wherein the mandrel has a shape based on a biological organ of a patient.

9. The method of claim 7, wherein the mandrel has a shape determined by a computer model.

10. The method of claim 7, wherein the mandrel is a collapsible mandrel.

11. The method of claim 7, wherein the particulate material is a water soluble salt, a water soluble sugar, a water soluble hydrogel, or any combination thereof.

12. The method of claim 7, further comprising treating the polymer network with a treatment selected from the group consisting of washing in a solvent, drying with a gas stream, sterilizing, sintering, and treating with a plasma discharge.

* * * * *